United States Patent
Arroyo et al.

[19]

[11] Patent Number: 5,843,388
[45] Date of Patent: Dec. 1, 1998

[54] STERILIZATION RACK FOR MEDICAL INSTRUMENTS

[75] Inventors: Patrice A. Arroyo, Ridgefield Park; Joseph Del Boccio, Pal. Park, both of N.J.

[73] Assignee: K-Medic, Inc., Northvale, N.J.

[21] Appl. No.: 801,156

[22] Filed: Feb. 18, 1997

[51] Int. Cl.[6] ...................................................... A61L 2/26
[52] U.S. Cl. ..................... 422/300; 422/297; 211/70.6; 211/69; 206/369; 206/370; 433/77
[58] Field of Search .................................. 422/297, 300; 211/70.6, 60.1, 68, 69, 69.1, 70.3; 206/369, 370, 438, 63.5; 433/49, 77, 79

[56] References Cited

U.S. PATENT DOCUMENTS

| | | | |
|---|---|---|---|
| 1,965,032 | 7/1934 | Davey | 211/69 |
| 2,616,558 | 11/1952 | Kay, Jr. | 211/70.3 X |
| 4,191,291 | 3/1980 | Brown | 422/297 X |
| 4,947,984 | 8/1990 | Kaufman et al. | 211/60.1 X |
| 5,193,672 | 3/1993 | Long | 422/300 X |
| 5,325,974 | 7/1994 | Staehs | 211/60.1 |
| 5,358,112 | 10/1994 | Gardner | 211/69 X |
| 5,451,380 | 9/1995 | Zinnanti | 422/300 |

*Primary Examiner*—Robert J. Warden
*Assistant Examiner*—E. Leigh McKane
*Attorney, Agent, or Firm*—Hughes Hubbard & Reed LLP; Ronald Abramson; Peter A. Sullivan

[57] ABSTRACT

An instrument rack for the sterilization and storage of surgical instruments within autoclave devices includes a bumper plate made from durable CECLON plastic, which is attached to the underside of the rack's top panel, to prevent the delicate sharp ends of surgical instruments from hitting the top of a metal rack when the rack is turned upside down. Therefore the edges of the instruments stay sharper longer and the instruments require less frequent repairs and sharpening. A "tent-like" or angled plate is attached to the rack's bottom panel, is constructed integral with the bottom panel, to prevent instruments from tilting outward or falling out of the rack when the "gate," which otherwise holds the instruments in place, is open. The angle of the tent or panel forces instruments to tilt toward the inside of the rack.

19 Claims, 6 Drawing Sheets

STERILIZATION RACK FOR MEDICAL INSTRUMENTS

FIELD OF THE INVENTION

The present invention relates to storage racks for holding medical and dental instruments during sterilization of the instruments within an autoclave sterilization apparatus, for storage of the instruments after sterilization. The storage rack can also be used to hold and dispense instruments in a surgical operation room.

BACKGROUND OF THE INVENTION

To house instruments during the autoclaving process, and to store instruments after autoclaving, there are different styles of racks for different types of instruments. All have same basic function and purpose, namely to hold a variety of instruments within a sterile enclosure, such as an autoclave apparatus, wherein the instruments are subject to a sterile inducing environment of heat and other physical conditions. While some of them have a locking mechanism to hold arms/gates in place, none of the existing racks have a simple novel base to hold instruments in place, without the need for complicated locking fasteners, nor do the existing racks provide protection of the instrument tips from abrasive wear and tear.

There are many problems with existing racks. For example, instruments can fall out of the racks because gates don't always lock securely. Also, many racks have metal slots which can damage instruments by scratching, which can cause burrs, blemishes, etc. on the surfaces of the instruments. Moreover, when racks are wrapped for sterilization they are often turned upside down, thus causing metal to metal contact between the tips of instruments and the top of rack. This can damage the sharp ends of osteotomes, curettes, chisels, elevators and gouges, etc. Existing racks are also difficult to load and unload. If the racks are loaded while standing upright, or if the gates are raised while upright, instruments are likely to fall or tip out. In addition, it is not easy to identify what instruments each rack holds.

To solve these problems, Applicants' assignee KMedic, Inc. of Northvale, N.J., designed improved racks wherein gates are held securely in place with side locking latches. The locking gates help prevent rack from opening accidentally. Furthermore the gates are covered with nylon coating, which helps protect instruments. All the slots are covered with nylon coating, to prevent scratching, to reduce chances of burrs and to prolong instrument life. Scratches can lead to corrosion which shortens the useful life of instruments. Burrs can easily puncture rubber gloves causing a potential hazard to a surgeon.

Among background art patents for containers/cassettes/trays for sterilization of surgical instruments include U.S. Pat. No. 4,135,868 of Schainholz; U.S. Pat. No. 5,215,726 of Kudla et al; U.S. Pat. No. 5,284,632 of Kudla et al, and U.S. Pat. No. 5,492,671 of Krafft.

While these references are all concerned with sterilizer containers, cassettes, or trays for surgical instruments, or the like, and for the protection of the instruments during handling as part of the sterilization process, none of the references solve the above noted problems in an apparatus that holds instruments in an upright, vertical position.

For example, Schainholz '868 describes a tray with a hinged cover having resilient deformable members to hold instruments in place. Kudla '726 and Kudla '632 both require complicated moving parts, such as rotatable clamping members. Krafft '671 requires separate holding brackets with complicated, irregular cut-out members for insertion of instruments therein. None of these are racks that stand up. They are only useful for flat storage.

OBJECTS OF THE INVENTION

It is therefore an object of the present invention to provide various lightweight racks for sterilization and storage of medical or dental instruments.

It is also an object to provide such a rack with holding brackets which help avoid metal to metal contact.

It is also an object to provide a sterilization rack for instruments which help protect sharp tips from being damaged.

It is yet another object to provide a sterilization rack which stays locked and prevents instruments from falling out, even when turned upside down.

It is also an object to provide a sterilization rack for instruments with a novel base which keeps instruments in a generally upright tilted position during loading and unloading.

It is also an object of the present invention to provide a sterilization rack which can also be used to dispense/hold instruments in the operating room where surgeon can easily remove one instrument at a time.

It is yet another object to provide a sterilization rack for instruments which holds instruments secure, yet is simple and quick to load and unload in an upright position.

It is yet another object to improve over the disadvantages of the prior art.

SUMMARY OF THE INVENTION

In keeping with these objects and others which may become apparent, the present invention includes a sterilization rack for holding instruments during sterilization and for storage, wherein a unique nylon coated "tent" or angled panel feature has been added to the base of each rack to retain the instruments in place. The instruments will not fall out when the gate is open. This eliminates the likelihood of instruments being damaged due to falling out of rack and is safer for health care workers because they will not be struck by tilted or falling instruments. It makes it easier to load and unload. The racks can be loaded and unloaded in the upright position and the instruments therein can be easily taken out one at a time. This is an important feature which enables the rack to go directly from storage to the operating room. The surgeon can remove instruments one at a time from the rack. Since it stands upright, the rack takes up less valuable table space in the operating room.

To alleviate the problems when the tips of instruments come into contact with metal when rack is turned upside down, a soft bumper plate, such as for example of ⅛" thick sterilizable material, such as a sterilizable plastic, for example, CELCON (acetal co-polymer), is attached to the underside of the top panel of the rack. When the rack is turned upside down, the instruments may shift and contact the soft bumper plate. However, a sterilizable material, such as CELCON (acetal co-polymer) plastic, is a material that is softer than stainless steel and it will not damage the sharp edges of stainless steel instruments. While some scoring and scratching will occur in the plastic plate, damage to the plastic plate will be minor and will not affect its function. The plastic plate is attached by recessed rivets to the top panel. The plate is attached loosely by a floating design with elongated holes, to the top panel of the rack to allow for expansion and contraction during the autoclave sterilization process.

Furthermore, to solve the problem that instruments can tilt outward and/or fall out when gate is opened, in several embodiments an angled retaining unit in the shape of a tent, with two upwardly extending side members meeting at a common edge, has been added to the bottom of each rack. These racks open on either side, so each angled side accomodates part of a set of instruments.

In an alternate embodiment, which opens on one side only, the retaining unit includes one angled upwardly extending cantilevered member, which is added to the bottom of each rack. In this embodiment, the entire set of instrument is angled toward one side of the rack.

In the tented embodiment, each angled retaining unit is constructed with a top angle of about 90 degrees and a side angle of about 45 degrees. Preferably, these angles do not vary more than 2 degrees but the angles can vary up to about 5 degrees. The angle of the side members of the tent-shaped retaining unit forces the top of instruments to tilt toward the inside of the rack. Each instrument pivots about a pivot point located within a slot within the lowermost bracket joining the two upwardly extending side panels of the rack.

This instrument orientation feature is in contrast to other prior art racks and containers which have flat bottom panels which do not influence the direction of instruments. This tent-shaped configuration of the angled retaining unit above the bottom panel is very effective in preventing instruments from leaning and/or falling out of racks when the racks are on a level surface.

Furthermore, the angled side members of the retaining unit are positioned at about a 45 degree angle to the vertical instrument axis.

The bottom of the instrument rests on 45 degree angle panel forcing the bottom instrument handle down and outward. The rack's lowest handle-holding cross bracket acts as a pivot point to tilt the top of the instrument toward the inside of the rack.

The design of the 45 degree angle panel and lowest handle-holding cross bracket varies to accommodate a variety of instrument styles.

The top and bottom panels are securely riveted in place, and the positioning slots in the cross brackets are sturdier and less likely to bend. Therefore, the racks will last longer. The positioning cross brackets have deeper slots to hold instruments in place better. Notches have been added to the top of each side panel, to insure that gates stay up during unloaded/loading of instruments. This helps prevent the gates from falling down accidentally. Moreover, each rack may bear a indicia chart which identifies what instrument type(s) each rack holds to assist in reducing loading time.

DESCRIPTION OF THE DRAWINGS

The present invention can best be understood in conjunction with the accompanying drawings, in which.

DETAILED DESCRIPTION OF THE PREFERRED EMBODIMENT

Figure 1:
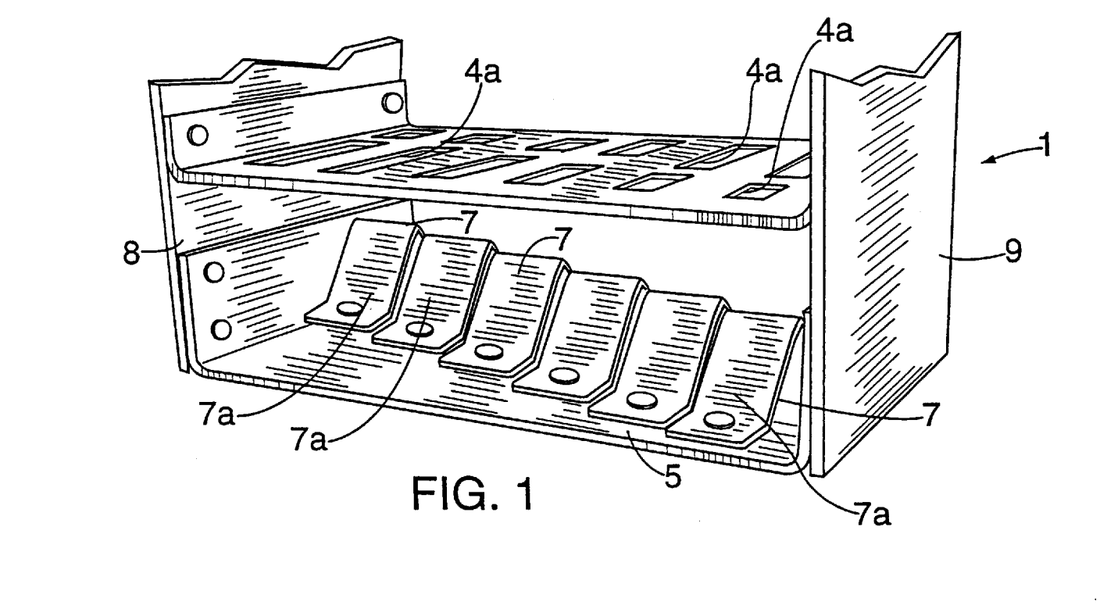
FIG. 1 is a perspective cut away view of one embodiment for a double-sided rack of the sterilization rack of the present invention, shown with a plurality of angled staggered instrument support members.
Figure 2:
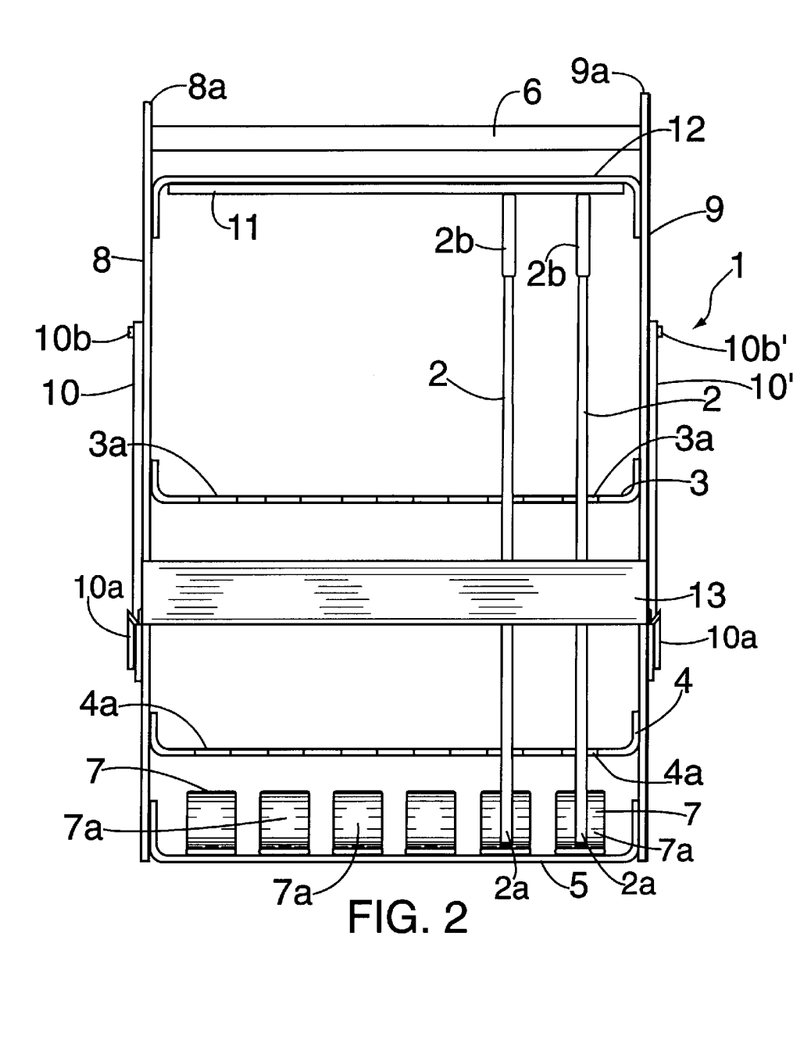
FIG. 2 is a front elevational view of the rack as in FIG. 1.
Figure 2A:
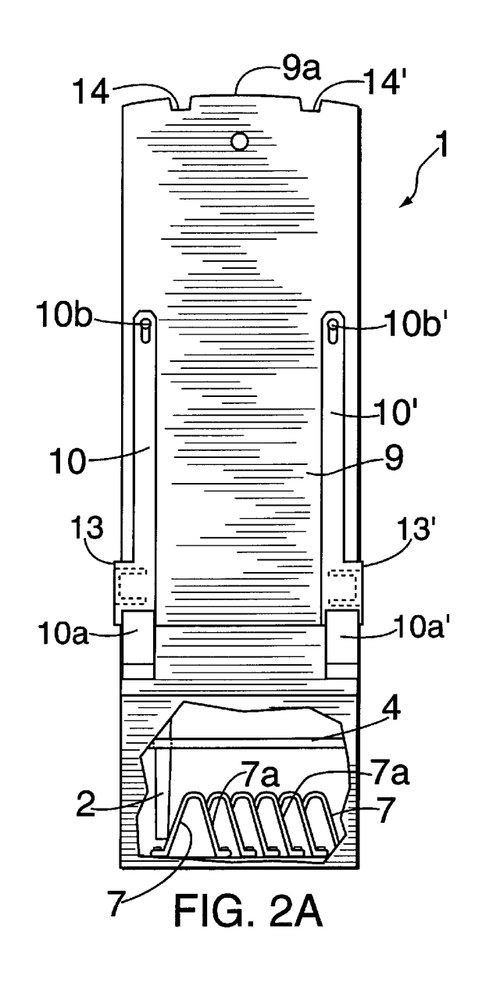
FIG. 2A is a side elevational view in partial cutaway section of the rack to show cutaway of pivot point on lowest cross bracket and nylon coated design of inside gates (13) as in FIG. 1.

FIGS. 1–2A illustrate a first embodiment for a double-sided sterilization rack 1 with various medical instruments 2 securely held therein in cross member brackets 3, 4 in accordance with the present invention. Sterilization rack 1 may include a base portion 5 and a corresponding top panel (12) and handle (6). Sterilization rack 1 also includes a plurality of instrumental retaining slots or holes 3a, 4a through brackets 3, 4 as is well known for use within sterilization racks. Slot members may be equally sized, or alternatively may include a set of slots, of one size and a further set or sets of slots of longer sizes. The slots may be staggered, due to the differing sizes of instruments.

Base portion 5 includes a plurality of support members 7 extending up from base portion 5. Support members 7 are substantially "tent" shaped with angled surfaces 7a, each surface 7a having varying side angles of about 45 degrees, and top angles of about 90 degrees, to accommodate and tilt inward various shapes and sizes of medical instruments 2, such as curettes, osteotomes, gouges, etc.

"Tent-like" or angled support members 7 are attached to the rack's bottom panel 5 as shown in FIGS. 1–2A or they may be constructed conceivably integral with the bottom panel 5 (not shown). Angled support members 7 prevent instruments 2 from tilting outward or falling out of sterilization rack 1 when either front gate 13 or rear gate 13', which otherwise hold instruments 2 in place, is open.

The angled panel 7 is positioned at about a 45 degree angle to the vertical axis of each instrument 2.

Figure 3:
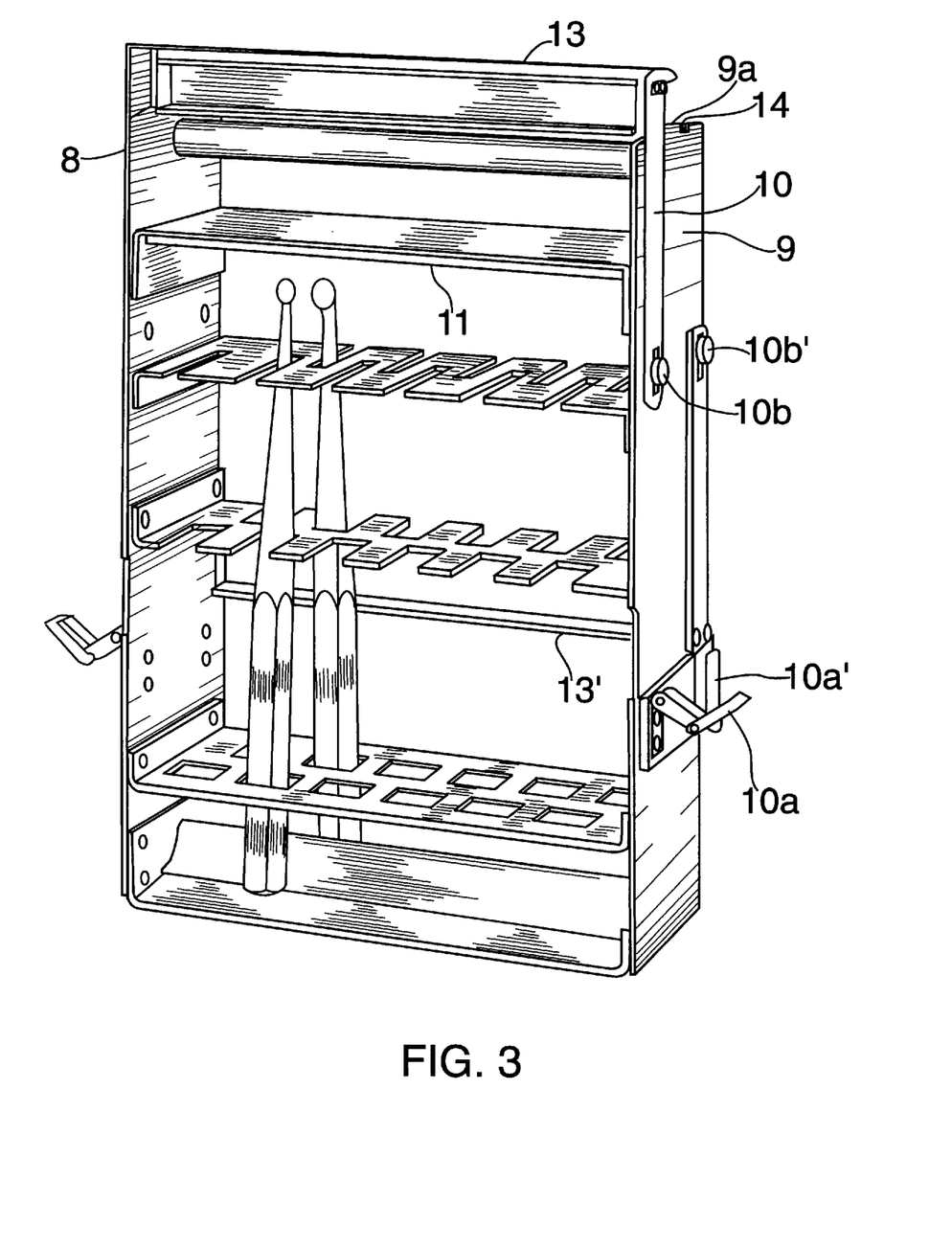
FIG. 3 is a perspective view of a first alternate embodiment of a rack, shown with one front gate in an open, upward position, and another rear gate in a closed, lowered position.
Figure 3A:
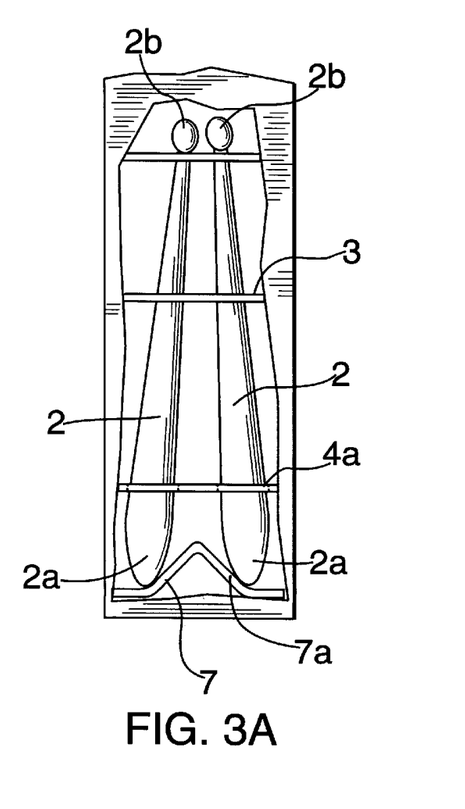
FIG. 3A is a side sectional view of a portion of the rack, shown with surgical instruments therein.

As shown in FIG. 3A, the bottom of the instrument 2 rests on 45 degree angle surface 7a of member 7 forcing the bottom instrument handle portion 2a of instrument 2 down and outward within the interior of sterilization rack 1. Each inside edge of slot 4a of the lowest handle-holding cross bracket 4 of rack 1 acts as a pivot point to tilt the top 2b of each instrument 2 toward the inside of rack 1.

Therefore, the angle of the tent-shaped angled support members 7 force tops 2b of instruments 2 to tilt toward the inside of sterilization rack 1, thus influencing the direction of instruments 2 and therefore preventing instruments 2 from leaning or falling out of sterilization rack 1. Tent-like support members 7 may be staggered to accommodate different instrument styles across base portion 5, as shown in FIG. 1.

The design of the 45 degree member 7 and the lowest instrument holding cross bracket 4 varies to accommodate a variety of instrument styles.

Figure 4:
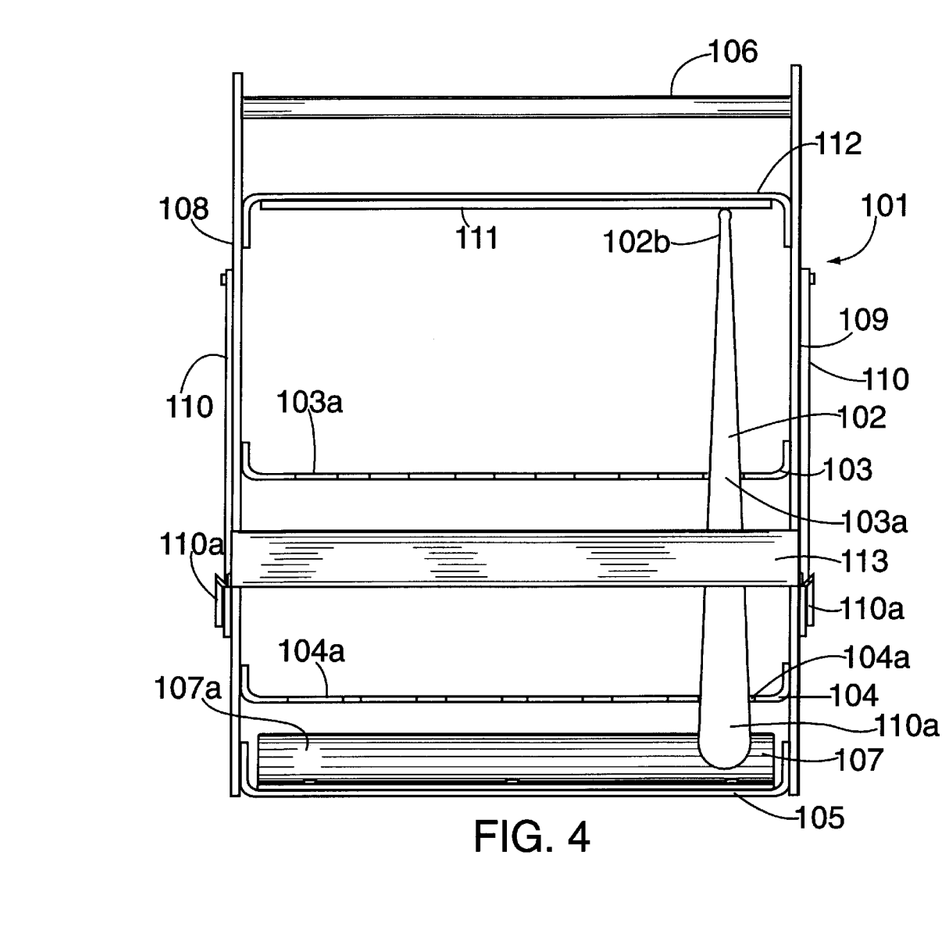
FIG. 4 is a front elevational view of a second alternate embodiment for a double sided rack of a sterilization rack with a continuous angled instrument support member.
Figure 5:
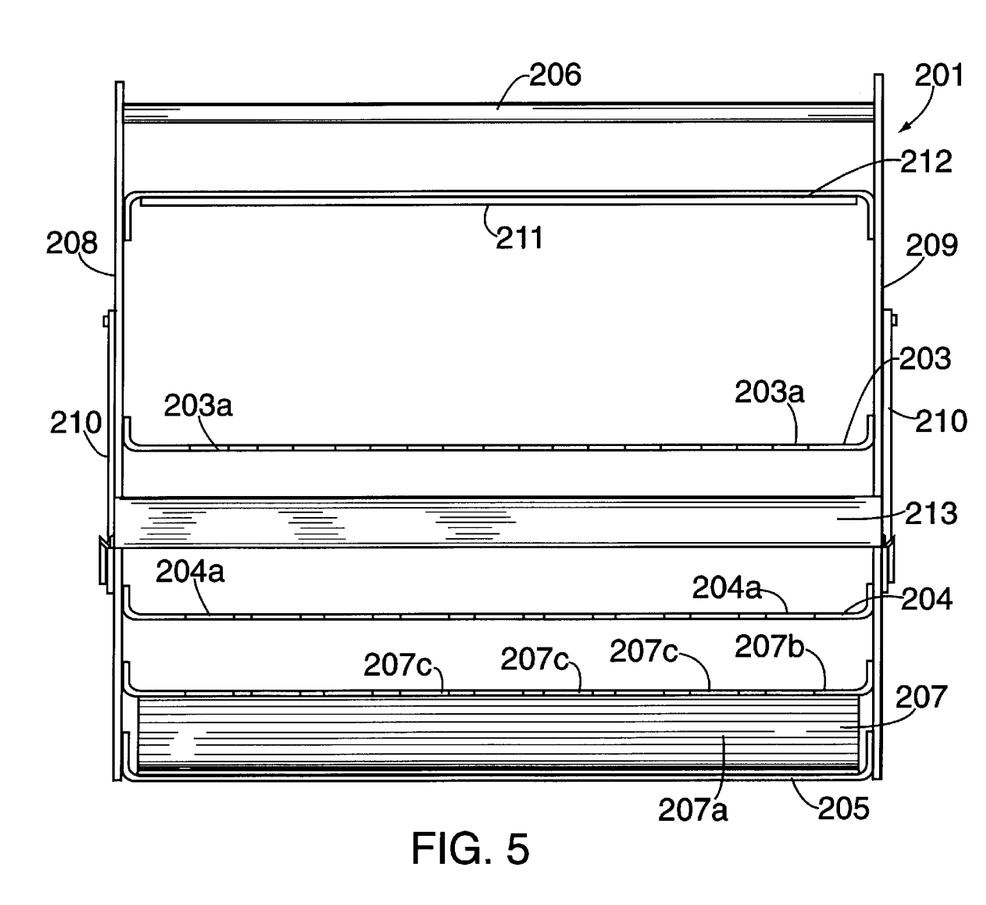
FIG. 5 is a front elevational view for a third alternate embodiment for a single sided rack of a sterilization rack with an angled support member extending downward from a slotted horizontal brace member.
Figure 6:
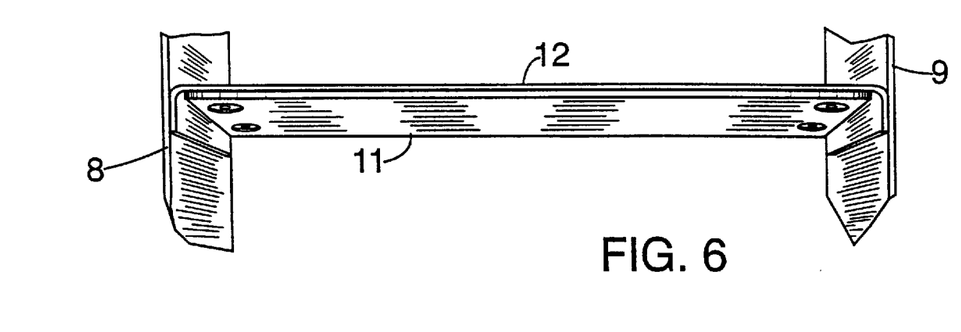

Furthermore, as shown in FIGS. 2, 3, 4, 5, and 6, in all embodiments instrument rack 1 includes a bumper plate 11, preferably about ⅛ inch in thickness, made from durable sterilizable material, such as a sterilizable plastic, for example, CELCON. Bumper plate 11 is attached to the underside of the top panel 12 of rack 1, which prevents the delicate sharp ends of surgical instruments 2 from hitting top panel (12) of sterilization rack 1 when sterilization rack 1 is turned upside down. Therefore the edges of instruments 2 will keep sharper longer and instruments 2 will require less frequent repairs and sharpening. Moreover, CELCON is a hard plastic which will not damage stainless steel instruments, such as instruments 2. Plastic bumper member 11 is attached by recessed rivets to the top panel 12 of the sterilization rack 1, as shown in FIG. 6.

The plate 11 is attached loosely by a floating design with elongated holes to allow for expansion and contraction during the sterilization process shown in FIG. 6.

Base portion 5 and handle bar 6 are separated by side panels 8, 9, which are secured by further brackets 3, 4, 12. Front gate lifting members 10 and rear gate lifting members 10', act to close front gate 13 and rear gate 13' respectively, after instruments 2 have been inserted within open slots 3a and closed slots 4a of cross member brackets 3, 4 of sterilization rack 1.

Figure 2B:
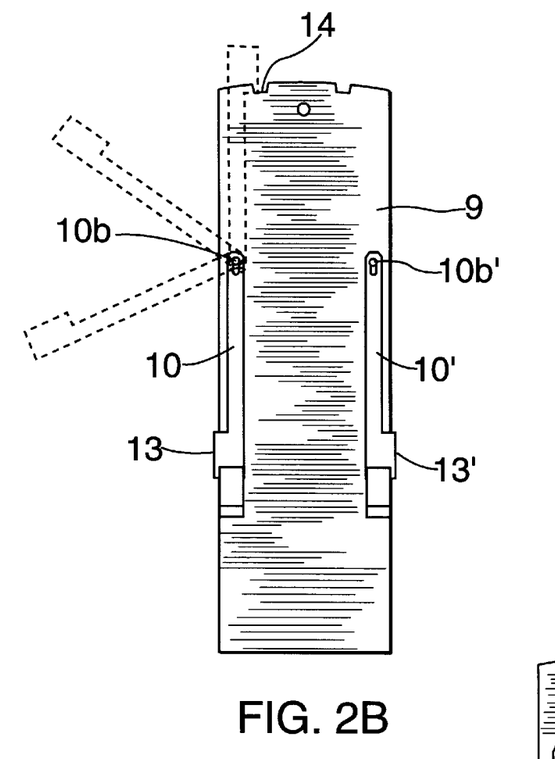
FIG. 2B is a side sectional view showing the rotational movement of a gate support member of the rack as in FIG. 1.

In the embodiment shown in FIGS. 2, 3 and 4, two gates 13, 13' are provided, closing the front and rear gaps between side panels 8, 9. Gate lifting members 10, 10' rotate above pivot points 10b, 10b', as shown in FIG. 2B, to lift gate 13, 13' up to the top edges 8a, 9a of side members 8, 9. Top edges 8a, 9a each contain at least one notch 14, or 14' to hold each gate 13 in an inverted position when rack is open for loading and unloading instrument 2, as shown in FIG. 3. Preferably front and rear notches 14, 14' are provided for both gates 13, 13'. Gate lifting members 10, 10' lock gates 13, 13' in place by means of side latches 10a, 10a' which secure gate 13, 13' in place in a closed position of the rack. FIG. 3 shows front gate 13 elevated in an open position and rear gate 13' lowered in a closed position.

To prevent scratching and burring of instruments 2, the inside facing surfaces of gates 13, 13' are preferably coated with an abrasion-resistant surface.

Top cross bar 6 is a rounded bar for easy carrying of racks.

Figure 4A:
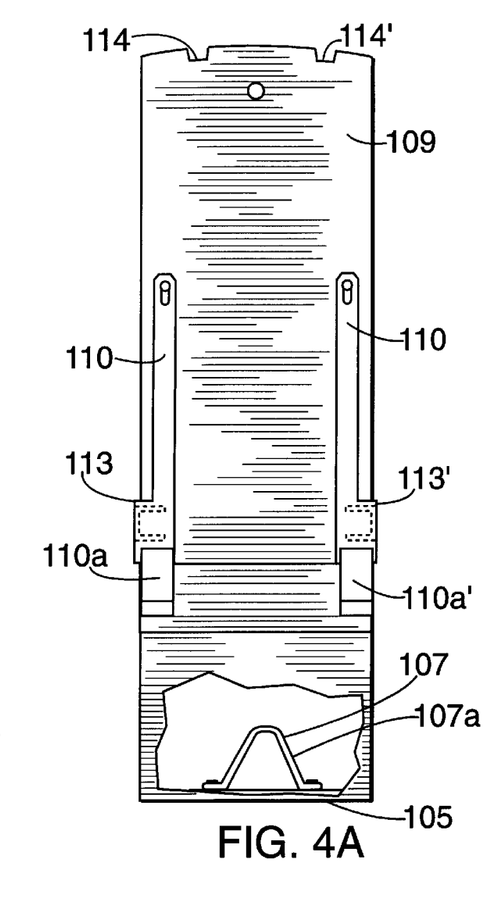
FIG. 4A is a side elevational view in partial cutaway section of the sterilization rack as in FIG. 4.

In a second alternate embodiment shown in FIGS. 4, 4A, instrument rack 101 includes side members 108, 109 separated by cross member brackets 103, 104. Reference numeral 112 represents the top panel, and reference numeral 106 represents the handle bar. Base member 105 supports a single continuously extending "tent like" angled support member 107 having two respective angled surfaces 107a, for tilting bottom instrument handles 102a outward and instrument tops 102b of instruments 102 inward. Instruments 102 are inserted within sterilization rack 101 when front gate 113 or rear gate 113' is opened, and instruments 102 are inserted within open slots 103a and closed slots 104a of brackets 103, 104. Gate support members 110, 110' act to close gates 113, 113' by swinging down and locking into place with respective front and rear side latches 110a, 110a'. To prevent abrasive damage to instruments 102, soft bumper member 111 extends under upper bracket 112, and the inward facing surfaces of gate 113, 113' may be coated with an abrasion resistant coating. Gate support members 110, 110' rotate and swing upwards towards notches 114, 114' about pivot points 110, 110' in a manner similar to gate support members 10, 10' shown in FIG. 3A.

Figure 5A:
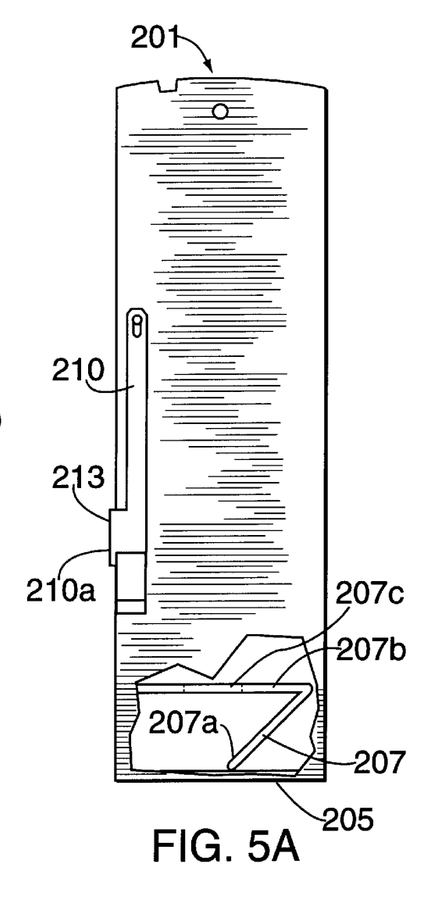
FIG. 5A is a side elevational view in partial cutaway section of the rack as in FIG. 5; and, FIG. 6 is a close-up perspective cutaway view of the soft upper bumper member of the racks shown in FIGS. 2, 3, 4 and 5 herein.

In a third alternate embodiment shown in FIGS. 5, 5A, single-sided instrument rack 201 includes side members 208, 209 separated by brackets 203, 204. Reference numeral 212 represents the top panel and reference numeral 206 represents the handle. Base member 205 supports a single continuously extending angled support member 207 having one angled surface 207a, for tilting the tops instruments (not shown) inward and the bottom side thereof outward. Angled support member 207 extends downwards from further cantilevered member 207b. In the embodiment shown in FIGS. 5, 5A, rack 201 opens on one front side only when gate 213 opens upwards. The instruments are inserted within sterilization rack 201 when gate 213 is opened. Furthermore, the instruments are inserted within slots 203a, 204a of brackets 203, 204, and slots 207c of cantilevered member 207b, from which cantilevered member 207b angled surface 207a extends down. Gate member 210 acts to close gate 213 on rack 201 by swinging down about pivot point 210b and locking into place with the side latch 210a. To also prevent abrasive damage to the instruments, soft bumper member 211 also extends under upper bracket 212.

Furthermore, it is known that other modifications may be made to the present invention, without departing from the scope of the invention, as noted in the appended claims. For example, there need only be at least one bracket between the side panels of the sterilization rack, wherein the at least one bracket includes one or more open or closed slots for insertion of an instrument therethrough. Moreover, the at least one bracket may alternatively include a further bracket having elastic bumper member thereon to prevent abrasive damage to tips of a medical or dental instrument.

We claim:

1. A sterilization rack for securely holding instruments therein comprising a base and a top panel separated by a pair of side panels with at least one holding bracket extending between said side panels, said at least one bracket including at least one slot defined by an opening therethrough, said at least one slot for receiving a medical instrument therethrough, an angled support member being provided at said base, and at least one openable gate, wherein said gate opens for insertion of the instruments into the slots.

2. The sterilization rack as in claim 1 wherein said at least one holding bracket includes a plurality of holding brackets.

3. The sterilization rack as in claim 1 wherein said at least one holding bracket includes a plurality of opened and/or closed slots, each said slot defining an opening for insertion of an instrument therethrough.

4. The sterilization rack as in claim 3, wherein said plurality of slots includes a group of said slots being larger than another group of said slots.

5. The sterilization rack as in claim 1 wherein said at least one bracket includes a further bracket located between said side panels at an opposite upper end from said base, said further bracket having an elastic bumper member on an underside thereof, said elastic bumper member isolating said further bracket from a tip end of the instrument to prevent abrasive damage thereto.

6. The sterilization rack as in claim 5, wherein said bumper member is a sterilizable plastic.

7. The sterilization rack as in claim 6, wherein said plastic is CELCON plastic.

8. The sterilization rack as in claim 5 wherein said elastic plate is loosely attached in a floating design to said further bracket.

9. The sterilization rack as in claim 1 wherein said at least one angled support member bears a tent-like shape.

10. The sterilization rack as in claim 1 wherein said at least one angled support member includes a plurality of angled support members.

11. The sterilization rack as in claim 10 wherein said plurality of angled support members are staggered across said base.

12. The sterilization rack as in claim 1 wherein said at least one angled support member includes a continuous angled surface extending at least partially across the width of said sterilization rack between said side panels.

13. The sterilization as in claim 1 wherein said as least one angled support member includes an angled surface extending from a cantilevered slotted member down toward said base.

14. The sterilization rack as in claim 1, wherein said at least one slot is coated with a non-abrasive coating.

15. The sterilization rack as in claim 14, wherein said non-abrasive coating is nylon.

16. The sterilization rack as in claim 1 wherein said angled support member has a top angle of about 90 degrees and an angle formed between said angled support member and said base of about 45 degrees.

17. The sterilization rack as in claim 1, wherein said openable gate includes a retaining member supported by at least one pair of rotatable support members, said rotatable supporting members rotating said gate upward from a closed, lowered position to an opened, upward position.

18. The sterilization rack as in claim 17, wherein said openable gate is inserted within at least one notch at a top end of each side panel.

19. The sterilization rack as in claim 17, wherein said at least one retaining member is secured in place by a locking latch.

* * * * *